(12) United States Patent
Heise et al.

(10) Patent No.: US 11,685,765 B2
(45) Date of Patent: *Jun. 27, 2023

(54) TANGENTIAL FLOW FILTRATION PROCESS FOR CONCENTRATING BIOMOLECULE SOLUTIONS

(71) Applicant: Fujifilm Diosynth Biotechnologies UK Limited, Billingham (GB)

(72) Inventors: Charles Heise, Billingham (GB); Tibor Nagy, Billingham (GB)

(73) Assignee: Fujifilm Diosynth Biotechnologies UK Limited, Billingham (GB)

(*) Notice: Subject to any disclaimer, the term of this patent is extended or adjusted under 35 U.S.C. 154(b) by 194 days.

This patent is subject to a terminal disclaimer.

(21) Appl. No.: 17/152,874

(22) Filed: Jan. 20, 2021

(65) Prior Publication Data

US 2021/0163530 A1  Jun. 3, 2021

Related U.S. Application Data

(63) Continuation of application No. 16/068,387, filed as application No. PCT/GB2016/053980 on Dec. 19, 2016, now Pat. No. 10,934,325.

(30) Foreign Application Priority Data

Jan. 7, 2016  (GB) ...................... 1600287

(51) Int. Cl.
*C07K 1/34* (2006.01)
(52) U.S. Cl.
CPC ...................... *C07K 1/34* (2013.01)

(58) Field of Classification Search
CPC .......... C07K 1/34; B01D 63/02; B01D 61/14; B01D 61/20; C12P 21/02
See application file for complete search history.

(56) References Cited

U.S. PATENT DOCUMENTS

| | | | | |
|---|---|---|---|---|
| 3,726,613 A | * | 4/1973 | von Casimir | F04B 11/0075 417/477.1 |
| 3,826,593 A | * | 7/1974 | Von Casimir | F04B 11/0075 417/477.1 |
| 3,951,377 A | * | 4/1976 | Milroy | F16K 7/18 251/35 |

(Continued)

FOREIGN PATENT DOCUMENTS

| | | |
|---|---|---|
| WO | 03/033120 A1 | 4/2003 |
| WO | 2009/010269 A1 | 1/2009 |

(Continued)

OTHER PUBLICATIONS

U.S. Appl. No. 61/983,186 filed by Oleg Shinkazh (Year: 2014).
(Continued)

*Primary Examiner* — Chester T Barry
(74) *Attorney, Agent, or Firm* — Banner & Witcoff, Ltd.

(57) ABSTRACT

A method of concentration of a liquid comprising a biomolecule is provided. The method comprises passing the liquid through a tangential flow filtration device under pressure, wherein the pressure applied is varied between at least a higher pressure and a lower pressure. Preferably, the variation in pressure is delivered by the use of a variable flow-controller, such as a valve.

15 Claims, 1 Drawing Sheet

(56) References Cited

U.S. PATENT DOCUMENTS

| | | | | |
|---|---|---|---|---|
| 4,037,818 | A * | 7/1977 | Soderberg | F16K 5/0605 |
| | | | | 251/304 |
| 4,492,531 | A * | 1/1985 | Kenji | A61M 60/853 |
| | | | | 417/279 |
| 6,011,148 | A * | 1/2000 | Bussey | C07H 1/06 |
| | | | | 536/25.4 |
| 6,062,829 | A * | 5/2000 | Ognier | F04B 43/1253 |
| | | | | 604/153 |
| 7,682,511 | B2 * | 3/2010 | de los Reyes | B01D 63/08 |
| | | | | 210/321.74 |
| 10,195,550 | B2 * | 2/2019 | Steen | B01D 61/147 |
| 10,934,325 | B2 * | 3/2021 | Heise | C07K 1/34 |
| 2003/0141480 | A1 * | 7/2003 | Green | F16K 27/067 |
| | | | | 251/315.01 |
| 2004/0256329 | A1 | 12/2004 | Meserol et al. | |
| 2007/0151924 | A1 | 7/2007 | Mir et al. | |
| 2007/0151925 | A1 * | 7/2007 | de los Reyes | B01D 61/16 |
| | | | | 210/321.72 |
| 2014/0263045 | A1 | 9/2014 | Mazumdar et al. | |
| 2015/0183815 | A1 | 7/2015 | Kopf et al. | |
| 2017/0298145 | A1 * | 10/2017 | Verkade | A61K 47/6889 |
| 2018/0296680 | A1 * | 10/2018 | Webber | A61K 47/545 |
| 2018/0340010 | A1 * | 11/2018 | Hug | A61C 5/68 |
| 2019/0046617 | A1 * | 2/2019 | Hanna | C07K 14/81 |
| 2019/0277815 | A1 | 9/2019 | Shinkazh | |

FOREIGN PATENT DOCUMENTS

| | | |
|---|---|---|
| WO | 2015/133972 A1 | 9/2015 |
| WO | 2015/164511 A1 | 10/2015 |

OTHER PUBLICATIONS

Chargraff, et al., "The chemical constituents of blood platelets and their role in blood clotting, with remarks on the activation of clotting by lipids" in "Studies on teh Chemistry of Blood Coagulation." (1936) downloaded Apr. 23, 2020 from www.jbc.org (Year: 1936).

* cited by examiner

TANGENTIAL FLOW FILTRATION PROCESS FOR CONCENTRATING BIOMOLECULE SOLUTIONS

RELATED APPLICATIONS

This application is a continuation of U.S. application Ser. No. 16/068,387, filed Jul. 6, 2018, now issued as U.S. Pat. No. 10,934,325, which is a National Stage Application under 35 U.S.C. 371 of co-pending PCT application PCT/GB2016/053980 designating the United States and filed Dec. 19, 2016; which claims the benefit of GB application number 1600287.5 and filed Jan. 7, 2016 each of which are hereby incorporated by reference in their entireties.

The present invention concerns a method for concentrating solutions of biomolecules, especially recombinant polypeptides and nucleic acids, and apparatus for carrying out such a method.

Many biomolecules, especially recombinant polypeptides and nucleic acids, such as plasmid DNA (pDNA), have attracted much attention in particular for therapeutic applications. Such biomolecules are commonly produced by culturing recombinant host cells which have been engineered to express the desired biomolecule. The biomolecule is then recovered from the culture medium by methods typically comprising centrifugation, filtration, and chromatographic purification. The recovery of the biomolecule commonly comprises the adjustment of the nature and properties of the liquid medium in which the biomolecule is dissolved or suspended. The processing involved typically generates relatively dilute solution of the biomolecule and hence increasing the concentration of the biomolecule in the medium during the recovery from the culture medium and purification may be desirable because, for example, the concentration may be so low that the use of the biomolecule is impractical in that form, or the storage of large amount of liquid would be required.

Conventional concentration processes involve the passing of an initial medium comprising the biomolecule through a filtration apparatus such as microfiltration or ultrafiltration membranes under constant pressure. Such apparatus is selected such that the biomolecule is retained in the retentate, but that a portion of the medium passes through the filtration medium to waste. The retentate is recirculated to a holding tank and the recirculation process continued until the desired concentration of biomolecule is attained. The disadvantage of such a process is that the concentration step is relatively slow, and hence slows down the processing of the biomolecule. Additionally, protein instability or insolubility (such as aggregation or denaturation) can occur due to the biomolecules repeatedly passing through the pump head and experiencing physical shear forces across a broad range of solute and buffer concentrations as the buffer exchange progresses. Further, conventional concentration processes involve large hold-up volumes. It would be desirable if the concentration step could be achieved in-line, as part of the processing of the biomolecule, instead of requiring batched recirculation-based concentration.

Figure 1:
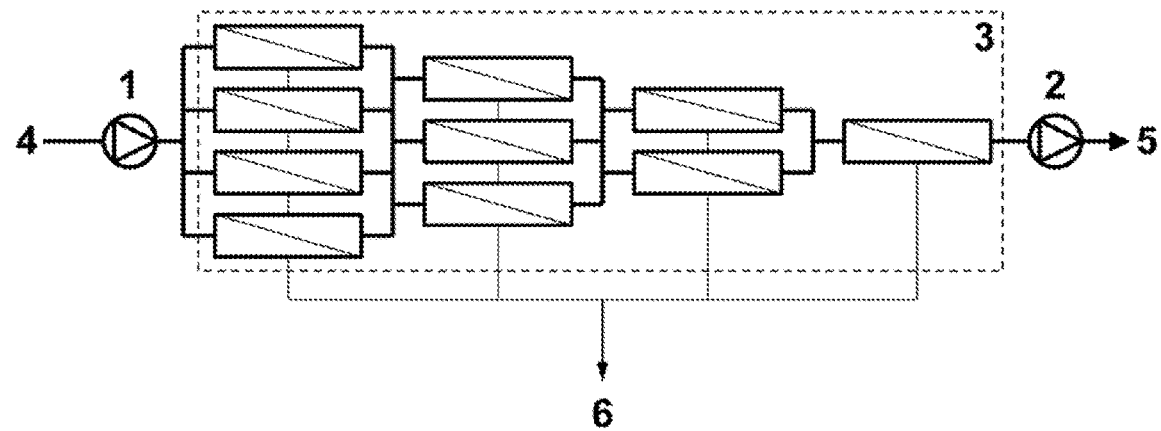
FIG. 1 depicts a prior art multiple tangential flow filtration device.

U.S. Pat. No. 7,682,511 describes a concentration method and apparatus wherein multiple tangential flow filtration devices are connected in "Christmas tree" configuration, as illustrated in FIG. 1, with flow through the devices being regulated by a combination of two pumps, one located upstream, 1, and one downstream, 2, of the filtration devices, 3, to control the flow rates of the feed, 4, and retentate, 5. Excess liquid is removed to the permeate, 6. Constant pressure is employed.

According to a first aspect of the present invention, there is provided a method of concentration of a liquid comprising a biomolecule which comprises passing the liquid through a tangential flow filtration device under pressure, wherein the pressure applied is cycled between at least a higher pressure and a lower pressure.

In one embodiment of the present invention, the method is carried out in-line, in which the retentate is not recirculated. The retentate is either used, or taken on for further processing. In other embodiments, the method is carried out in batch or partial batch mode, where some or all of the retentate is recirculated to the feed.

Tangential flow filtration ("TFF") devices that can be employed in the apparatus are well known in the art (see for example Filtration in the Biopharmaceutical Industry, ed. T. H. Meltzer and M. W. Jornitz, 1998) and include flat sheet, hollow fibre and annular wound devices. Preferably, the TFF device is a hollow-fibre filtration device.

The TFF device is selected to have a cut-off appropriate to the nature of the biomolecule, such that the biomolecule does not pass through a barrier, whereas smaller components of the liquid can pass through the barrier to the permeate.

It will be recognised that the extent of the differential between the higher and the lower pressure is dependent upon the conditions employed. For example, all other things being equal, operating at a higher feed flow rate will result in a larger differential than operating at a lower feed flow rate. Similarly, for hollow fibres, higher shear rates will result in a larger pressure differential than lower shear rates.

The upper limit of the pressure employed in the present application is the operating limit for the apparatus employed. In certain instances, the upper limit may be selected to be the operating limit of the device specified by the manufacturer. It will be recognised that the practical upper limit for the higher pressure may be significantly higher than that specified by the manufacturer and can readily be determined through routine experimentation. In many embodiments, the higher pressure is at least 25%, for example at least 30%, such as at least 40%, commonly at least 50%, typically at least 60%, often at least 70%, preferably at least 80% and may be at least 90% of the operating limit.

In certain embodiments, the lower pressure is no more than 40%, commonly no more than 30%, typically no more than 20%, and preferably no more than 10% of the operating limit.

In some embodiments, the difference between lower and higher pressure is selected to be greater than 5% of the higher pressure. In certain embodiments, the difference between lower and higher pressure is selected to be in the range of from greater than 5 to 50% for example from 10 to 40%, of the higher pressure. In other embodiments, the difference between lower and higher pressure is selected to be within the range of from greater than 50 to 95%, for example from 70 to 90% of the higher pressure.

In many especially preferred embodiments, the higher pressure is at least 1.05 fold greater than the lower pressure. In some especially preferred embodiments, the higher pressure is from at least 1.1 to 2.0 fold greater than the lower pressure. In other especially preferred embodiments, the higher pressure is from 2 to 10 fold, particularly from 3 to 7 fold greater than the lower pressure.

The method of the first aspect of the invention may involve applying for example two, three, four or more different pressures, the highest and the lowest pressures applied being as described above, and any other pressure applied being intermediate between these. In certain embodiments where two different pressures are employed, the higher pressure is applied for up to 99.9%, such as up to 99%, 98%, 97%, 96%, 95%, 94%, 93%, 92%, 91% or 90% of the total process time, and the lower pressure for the remainder. In many instances, the higher pressure is applied for at least 50% of the total process time, often at least 60%, such as at least 70%, and preferably at least 80% of the total process time, and the lower pressure for the remainder. In many preferred embodiments, the higher pressure is applied for from 85 to 99% of the total process time, and the lower pressure for the remainder.

In many embodiments, when the TFF device is a hollow fibre device, the operating limit is typically approximately from 2 to 4 bar, and when the TFF device is a flat sheet device, the operating limit is typically approximately from 5 to 7 bar.

It will be recognised that, all other things being equal, the length of the TFF device employed will influence the concentration factor that can be achieved, such that the longer the fluid path length within the concentrator, the greater the concentration factor. The ratio of the total membrane area to the total effective width in the case of flat sheet devices or circumference in the case of hollow fibre devices will influence the concentration factor. Larger ratios will result in a greater concentration factor than smaller ratios for the same membrane area. In certain embodiments, the length of the path is selected to be greater than 30 cm, especially greater than 40 cm, and preferably greater than 50 cm. In many instances, the length of the path is up to 200 cm.

Means of applying pressure to the TFF device are well known in the art, and include the application of gas pressure, especially an inert gas, such as nitrogen or helium. Preferably the means for applying pressure is a pump. Pumps which can be employed include peristaltic, diaphragm, lobe and centrifugal pumps. Both disposable and re-usable pump designs can be employed. The means for applying pressure may be employed with a flow restrictor located downstream of the TFF device. Examples of flow restrictors include pinch valves. In many preferred embodiments, the flow restrictor comprises a variable flow valve.

Restrictors which may be employed in the present invention serves to regulate the flow of the liquid through the TFF device, and hence in combination with the means for imparting flow to control the pressure applied to the liquid in the TFF device, and hence the relative proportions of the liquid in the retentate and the permeate, and hence the concentration factor achieved.

When the flow restrictor is a fixed restrictor, the pressure applied can be varied by regulating the flow rate of liquid through the TFF device, for example by increasing and decreasing the speed of the pump, or increasing or decreasing the gas pressure applied.

When a variable flow valve is employed as a means to vary the applied pressure, the variable flow valve may regulate the flow between a first, relatively low flow rate wherein the liquid remains able to flow and at least a second, higher flow rate. In preferred embodiments, the variable flow valve is an intermittent flow valve, which prevents flow in a first position, but permits flow in at least a second position.

In certain preferred embodiments the flow of liquid through the variable flow valve is controlled by a programmable control unit which regulates the opening and closing of the valve in order to achieve the required concentration. This is achieved through cycling, with a pre-determined time period of relatively low flow rate and relatively higher flow rates, or, for example, opening and closing of the valve, to generate the desired concentration. One cycle represents the pressure changing from the original pressure to the higher or lower pressure, and returning to the original pressure, which equates to the steps of the valve opening and closing and returning to the initial state. The cycle rate can be either constant or varied. In many operating conditions, the cycle rate of the variable flow valve is maintained as a constant throughout the concentration process.

In many embodiments, multiple cycles are employed. The number of cycles employed will depend on numerous factors such as the duration of the process, the volume of liquid being concentrated, the flow rate, the maximum pressure of the apparatus, the length and/or area of the TFF device and the molecular weight cut-off for the TFF device. In certain embodiments, at least 10 cycles, such as at least 50, 100, 500, 750, 1000, 1500, 2000, 3000, 5000, 7500, 10000 or more cycles can be employed.

It will be recognised that a range of cycle frequencies can be employed. All other factors being equal, a higher frequency will produce a smaller difference between higher and lower pressures, whereas a lower frequency will produce a larger difference. Either may be advantageous in different circumstances depending on the nature of the process being carried out. In many instances, the frequency is less than 100 Hz, typically less than 50 Hz, commonly less than 10 Hz, and preferably less than 5 Hz. In certain preferred embodiments, the frequency is 2 Hz or less, most preferably 1 Hz or less, such as from 0.05 to 0.5 Hz.

When the variable flow valve is open, the liquid passes through the TFF device and valve to the retentate. When the said valve is closed the liquid passes through the TFF filter to the permeate and any solute and/or biomolecule greater than the cut-off of the TFF device is retained in the concentrator to be flushed to the retentate the next time the valve on the retentate line opens.

During the operation of a TFF device, it is common for a gel layer comprising biomolecule to form on the retentate side of the filter surface. This gel layer is typically removed from the TFF device by the inclusion of a flush at the end of the concentration, and such a flush step can be employed in the process of the present invention. A flush step at the end of the concentration can result in significant spike in the concentration of biomolecule, and therefore may result in a higher than expected biomolecule concentration. In certain embodiments of the present invention, flush stages are included at intervals throughout the concentration process. A flush stage may comprise extending the period at which the liquid passes through the TFF device at the lower pressure, and may additionally comprise prevention of permeate flow, such that all flow passes to the retentate such as by closing a valve on the permeate line, preferably for the duration of the flush. The duration of a flush stage is often selected to achieve transfer of substantially all of the gel layer into the retentate. A flush stage at the end of concentration may comprise passing up to five TFF device volumes. Flush stages included at intervals in the concentration process may comprise passing lower TFF device volumes, such as 0.25, 0.5, 0.75 or 1 TFF device volumes. In some embodiments, a flush stage is employed after operation of the cycling between a higher and a lower pressure for the passage of 1

TFF device volume, 2 TFF device volumes, 5 TFF device volumes, 10 TFF device volumes or more, followed by a return to operation of the cycling between a higher and lower pressure. In many embodiments where one or more flush stages are incorporated at intervals in the concentration process, the flush stage is accompanied by prevention of permeate flow, such as by closing a valve on the permeate line, preferably for the duration of the flush.

Liquids employed in the present invention may be eluent from purification methods (eg chromatography columns, conventional or single pass TFF steps, filtration/clarification steps, centrifuge supernatant/centrate or slurries, conditioning/dilution steps), output from bioreactors and fermenters, and output from cell disruption processes.

The apparatus according to the present invention can be employed for concentration of liquids comprising biomolecules, for example pDNA, inclusion bodies, particularly inclusion bodies comprising polypeptides, and especially recombinant polypeptides.

pDNA may be in one or more of multiple forms, such as supercoiled, linear and open-circular (i.e. nicked or relaxed) isoforms. Supercoiled pDNA isoform has a covalently closed circular form and the pDNA is negatively supercoiled in the host cell by the action of host enzyme systems. In the open-circular isoform, one strand of the pDNA duplex is broken at one or more places.

Methods for the production of pDNA are well known in the art. pDNA may be natural or artificial, for example, cloning vectors carrying foreign DNA inserts. In many embodiments, the pDNA is in the size range of 1 kilobase to 50 kilobases. For example pDNA encoding expressed interfering RNA is typically in the size range of 3 kilobases to 4 kilobases.

Polypeptides, especially recombinant polypeptides, include therapeutic proteins and peptides, including cytokines, growth factors, antibodies, antibody fragments, immunoglobulin like polypeptides, enzyme, vaccines, peptide hormones, chemokines, receptors, receptor fragments, kinases, phosphatases, isomerases, hydrolyases, transcription factors and fusion polypeptides.

Antibodies include monoclonal antibodies, polyclonal antibodies and antibody fragments having biological activity, including multivalent and/or multi-specific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$—$V_H$, $V_H$—$V_L$, or $V_L$—$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

Inclusion bodies include insoluble aggregates formed in the cytoplasm of bacterial cells such as *E. coli*, most commonly comprising polypeptide and especially recombinant polypeptide.

In addition to the biomolecule, other components of the liquid may include salts, including buffer salts, culture media and feed components, solvents, commonly water, zwittergens, surfactants, imidazole or other competitive ligand binders, amino acids, chaotropic agents, such as urea, reductants, oxidants, PEGylation conjugation reactants (substrates, by-products and activators), sugars, lipids, nucleic acids, metabolites and small polypeptides.

The method may be employed as a unitary operation, or may comprise one or more of the steps in a multi-step process. In some embodiments, a single concentration method according to the present invention is employed. In other embodiments, two or more concentration methods according to the present invention are employed. Where two or more concentration methods are employed, the steps may be in series, commonly separated by one or more purification or processing stages, such as chromatography, centrifugation, conventional filtration or buffer exchange. Two or more concentration methods may also be carried out in parallel, such as in concentrating different process streams which are subsequently combined, and which may be subsequently subject to further concentration by methods according to the present invention.

Liquids produced by the apparatus and processes of the present invention can be used "as is" with no further processing, or may be subject to one of more further processing steps, such as purification or processing steps, for example chromatography steps, such as affinity chromatography, anion and/or cation exchange chromatography, hydrophobic interaction chromatography, size-exclusion chromatography, affinity chromatography; and/or further filtration, clarification, conditioning, dilution or other formulation steps.

A method for the production of a biomolecule which comprises the method of the first aspect of the present invention forms a second aspect of the present invention.

According to a third aspect of the present invention, there is provided apparatus for in-line concentration of a biomolecule-containing liquid comprising a TFF device in fluid connection with a means for imparting flow of the liquid through the TFF device and a variable flow valve, wherein the means for imparting flow is located upstream of the filtration device, the variable flow valve is located downstream of the TFF device, and the variable flow valve is controlled to cycle between at least a higher pressure and a lower pressure.

TFF devices, means for imparting flow, variable flow valves, biomolecules and liquids employed in this aspect are as described above in respect of the first aspect of the present invention.

In some embodiments of the present invention, the apparatus comprises a single TFF device. In other embodiments, the apparatus comprises two or more TFF devices, which may be in series and/or in parallel. In certain embodiments, the apparatus comprises two or more TFF devices configured in accordance with the third aspect of the present invention in series, where the outlet from the upstream TFF device is in fluid connection with a downstream TFF device.

In a related aspect, there is provided a process for the concentration of a biomolecule in a liquid wherein the biomolecule is concentrated by the use of apparatus according to the first aspect of the present invention.

The concentration process may be employed as a unitary operation, or may comprise one or more of the steps in a multi-step process. In some embodiments, a single concentration step according to the present invention is employed. In other embodiments, two or more concentration steps according to the present invention are employed. Where two or more concentration steps according to the present invention are employed, the steps may be in series, commonly separated by one or more purification or processing stages, such as chromatography, centrifugation, conventional filtration or buffer exchange. Two or more concentration steps may also be carried out in parallel, such as in concentrating different process streams which are subsequently combined, and which may be subsequently subject to further concentration by processes according to the present invention.

Figure 2:
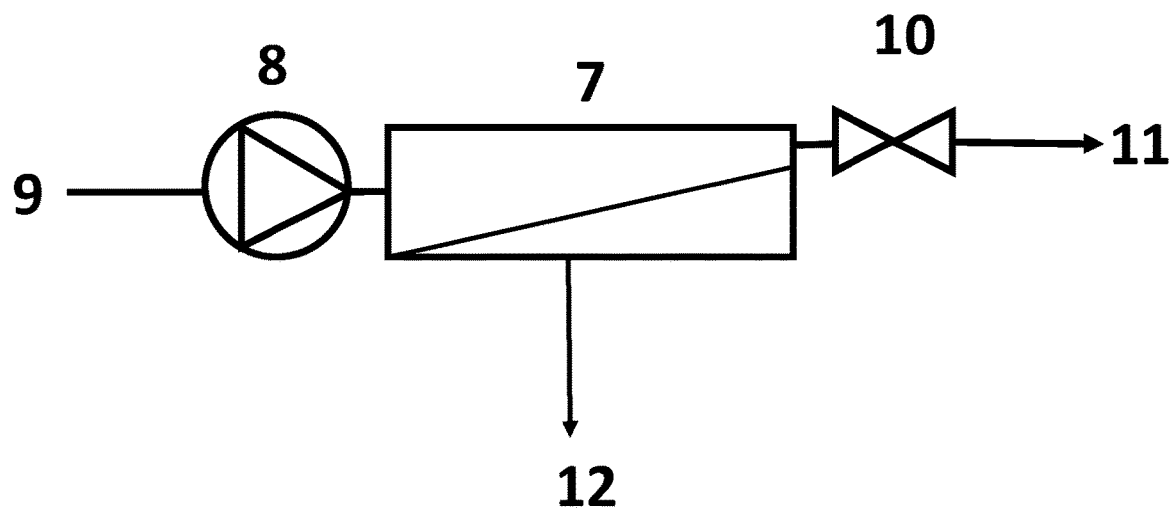
FIG. 2 depicts the present invention apparatus as disclosed herein.

Apparatus according to the present invention is illustrated in FIG. 2. A TFF device, 7, is located downstream of a pump, 8, which supplies a liquid feed, 9, to the TFF device, 7. An intermittent flow valve, 10, is located on the retentate line, 11. Cycling of the intermittent flow valve, 10, between closed or more restricted and open or less restricted positions causes a cycling of pressure across the TFF device, 7. When the valve, 10, is closed or restricted, the pressure increases, and liquid components smaller than the cut-off of the TFF device, 7 are forced into the permeate, 12, thereby increasing the concentration of the biomolecule. The biomolecule is retained in the TFF device, 7, and passes into the retentate, 11.

The present application is illustrated without limitation by the following examples.

Example 1

Abbreviations mPES modified Polyethylenesulfone
rhLactoferrin recombinant human Lactoferrin
VCF volumetric concentration factor A stock solution of purified rhLactoferrin at an initial concentration of 1 mg/mL in 25 mM sodium phosphate buffer, pH 7.5, was used in the experimental studies. The stock solution was volumetrically concentrated using a concentrator system comprising a GE Healthcare ÄKTA™ Explorer system with a Spectrum Labs Midkros™ hollow fibre concentrator (65 cm long, 10 kDa mPES hollow fibre having a surface area of 370 $cm^2$, maximum recommended operating pressure 2 bar). The hollow fibre retentate line was in turn directly connected to inlet valve 1 of a downstream variable flow-controller comprising a dual inlet variable flow-controller. The dual inlet variable flow-controller comprises of a custom made (Gemü) plastic, two valve manifold with a single outlet having a 2 mm internal bore with a fast acting solenoid actuator under the control of a Raspberry Pi minicomputer, which controls the flow of liquid through the manifold and through the concentrator. Inlet valve 2 of the dual inlet variable flow-controller remained fully closed throughout. The system was configured to run at a constant flow rate of 15 mL/min and the rhLactoferrin was directed in down flow mode through position 2 on the ÄKTA™ Explorer V2 valve into the concentrator. The flow rate of the hollow fibre retentate was regulated by the downstream inlet valve. The cycle time of the valve was set to 2 seconds and the valve controlled to be fully open for 5% of the cycle, and fully closed for the remaining 95% of the cycle, to provide a theoretical 20-fold VCF. The outlet from the intermittent flow valve was connected to valve V3, position 2 on the ÄKTA™ Explorer and the concentration of rhLactoferrin monitored by measuring 280 nm absorbance data. The in-line concentrated rhLactoferrin solution was collected through the outlet line F8 on the ÄKTA™ Explorer valve V4. The permeate from the hollow fibre was collected separately to determine the volumetric concentration factor. Maximum and minimum system pressures were recorded. The concentrator was flushed with buffer followed by 1 mg/mL rhLactoferrin with the retentate line fully open to prime the concentrator. To clear the concentrator of concentrated rhLactoferrin the retentate line was fully opened before the concentrator was flushed with buffer.

Examples 2 to 12

The method of Example 1 was repeated, but with the conditions varied as stated in Table 1. For Examples 8 to 12, longer hollow fibres of the stated lengths were employed.

The results of Examples 1 to 12 are given in Table 1.

TABLE 1

| Example | Concentrator length (cm) | % time valve open | Flow rate (mL/min) | Max Pressure (bar) | Max − Min Pressure (bar) | Achieved VCF |
|---|---|---|---|---|---|---|
| 1 | 65 | 5 | 5 | 1.0 | 0.2 | 6.2 |
| 2 | 65 | 5 | 15 | 2.5 | 0.3 | 7.4 |
| 3 | 65 | 12.5 | 10 | 2.2 | 0.3 | 4.7 |
| 4 | 65 | 12.5 | 15 | 1.9 | 0.5 | 3.4 |
| 5 | 65 | 20 | 5 | 1.8 | 0.3 | 2.7 |
| 6 | 65 | 20 | 15 | 2.6 | 0.5 | 3.7 |
| 7 | 65 | 25 | 15 | 1.3 | 0.4 | 2.7 |
| 8 | 105 | 15 | 10 | 0.6 | 0.5 | 2.8 |
| 9 | 150 | 5 | 15 | 0.8 | 0.3 | 10.8 |

TABLE 1-continued

| Example | Concentrator length (cm) | % time valve open | Flow rate (mL/min) | Max Pressure (bar) | Max − Min Pressure (bar) | Achieved VCF |
|---|---|---|---|---|---|---|
| 10 | 150 | 5 | 25 | 2.1 | 0.3 | 11.8 |
| 11 | 150 | 25 | 15 | 0.6 | 0.5 | 3.9 |
| 12 | 150 | 25 | 25 | 1.6 | 0.4 | 4.9 |

Examples 13 to 19

The method of Example 1 was repeated using a 2 mg/mL stock of IgG1 anti-CD20 monoclonal antibody, molecular weight approximately 150 kDa, with two 65 cm 50 kDa molecular weight cut off hollow fibres in series and the conditions varied as stated in Table 2.

The results of Examples 13 to 19 are given in Table 2.

TABLE 2

| Example | Concentrator length (cm) | % time valve open | Flow rate (mL/min) | Max Pressure (bar) | Max − Min Pressure (bar) | Achieved VCF |
|---|---|---|---|---|---|---|
| 13 | 130 | 21 | 10 | 1.8 | 0.4 | 4.9 |
| 14 | 130 | 11 | 10 | 1.8 | 0.4 | 5.4 |
| 15 | 130 | 1 | 10 | 1.8 | 0.4 | 125.2 |
| 16 | 130 | 11 | 15 | 2.1 | 0.3 | 3.9 |
| 17 | 130 | 21 | 20 | 1.2 | 0.4 | 4.2 |
| 18 | 130 | 11 | 20 | 1.9 | 0.3 | 4.2 |
| 19 | 130 | 1 | 20 | 2.4 | 0.3 | 8.8 |

The results showed an inverse linear relationship between the time the valve is open and the VCF achieved. Further, using a single 65 cm hollow fibre concentrator with an intermittent flow valve VCFs over 7-fold could be achieved. This is surprising as it is nearly double the VCF attainable by the PALL Cadence™ in-line concentrator, where the configuration of the 4-in line Cadence™ in-line concentrator gives a direct path length comparable to a 65 cm hollow fibre. A further surprise was that the flow rate had only a very small impact on the attainable VCF, thereby offering greater operational flexibility. All other factors being equal, increasing the length of the concentrator resulted in the attainment of higher concentration factors.

The invention claimed is:

1. A method of concentration of a liquid comprising a biomolecule which comprises passing the liquid through a tangential flow filtration device under pressure, wherein the pressure is applied by means of a pump, and the pressure is varied by operation of an intermittent flow valve, wherein the pressure applied is cycled between at least a higher pressure and a lower pressure, and wherein at least 10 cycles are employed.

2. The method according to claim 1, wherein the method is carried out in-line.

3. The method according to claim 1, wherein two different pressures are employed, the higher pressure being employed for up to 99.9% of the time of application of the pressure.

4. The method according to claim 1, wherein at least 1000 cycles are employed.

5. The method according to claim 1, wherein a cycle frequency of less than 100 Hz is employed.

6. The method according to claim 5, wherein the cycle frequency is from 0.05 to 0.5 Hz.

7. The method according to claim 1, wherein two different pressures are employed, and the higher pressure is at least 1.05 fold greater than the lower pressure.

8. A process for the production of a biomolecule which comprises concentration of a liquid comprising the biomolecule by a method according to claim 1.

9. A process for the production of a biomolecule which comprises concentration of a liquid comprising the biomolecule by a method according to claim 1.

10. A method of concentration of a liquid comprising a biomolecule which comprises passing the liquid through a tangential flow filtration device under pressure, wherein pressure is applied by means of a pump, and the pressure is varied by operation of a variable flow valve, two different pressures are employed, the pressure applied is cycled between a higher pressure and a lower pressure, at least 10 cycles are employed, the higher pressure being employed for from 85 to 99% of the time of application of the pressure, a cycle frequency of less than 5 Hz is employed, and the higher pressure is from at least 1.1 to 2.0 fold greater than the lower pressure.

11. The method according to claim 10, wherein the method is carried out in-line.

12. The method according to claim 10, wherein the variable flow valve is an intermittent flow valve.

13. The method according to claim 10, wherein at least 1000 cycles are employed.

14. The method according to claim 10, wherein the cycle frequency is from 0.05 to 0.5 Hz.

15. The method according to claim 11, wherein at least 1000 cycles are employed and the cycle frequency is from 0.05 to 0.5 Hz.

\* \* \* \* \*